United States Patent [19]

Denny

[11] Patent Number: 4,861,566

[45] Date of Patent: Aug. 29, 1989

[54] DESULPHURIZATION

[75] Inventor: Patrick J. Denny, Darlington, United Kingdom

[73] Assignee: Imperial Chemical Industries PLC, London, England

[21] Appl. No.: 126,499

[22] Filed: Nov. 30, 1987

Related U.S. Application Data

[63] Continuation-in-part of Ser. No. 876,747, Jun. 20, 1986, which is a continuation-in-part of Ser. No. 889,464, Jul. 25, 1986, Pat. No. 4,717,552.

[30] Foreign Application Priority Data

Dec. 24, 1986 [GB] United Kingdom ............... 8630846

[51] Int. Cl.$^4$ ............................................. C01B 17/16
[52] U.S. Cl. .................................. 423/230; 423/244; 423/220; 55/73
[58] Field of Search .............. 55/35, 75, 73; 423/230, 423/244, 220

[56] References Cited

U.S. PATENT DOCUMENTS

| | | | |
|---|---|---|---|
| 4,088,736 | 5/1978 | Courty et al. | 423/230 |
| 4,358,297 | 11/1982 | Eberly | 423/230 |
| 4,374,105 | 2/1983 | Anderson | 423/230 |
| 4,374,654 | 2/1983 | McCoy | 423/230 |
| 4,442,078 | 4/1984 | Jalan et al. | 423/230 |
| 4,522,793 | 6/1985 | Larson et al. | 423/230 |
| 4,533,529 | 8/1985 | Lee | 423/244 |
| 4,599,161 | 7/1986 | Scinta et al. | 423/244 |
| 4,673,557 | 6/1987 | Nieskens et al. | 423/230 |
| 4,717,552 | 1/1988 | Carnell et al. | 423/230 |

FOREIGN PATENT DOCUMENTS

| | | | |
|---|---|---|---|
| 2650711 | 10/1977 | Fed. Rep. of Germany | 423/230 |
| 87834 | 5/1985 | Japan | 423/244 |
| 1568703 | 6/1980 | United Kingdom | 423/230 |

Primary Examiner—Anthony McFarlane
Attorney, Agent, or Firm—Cushman, Darby & Cushman

[57] ABSTRACT

Fluid streams, particularly natural gas, are desulphurized by passage over a bed of a particulate absorbent containing zinc oxide at below 120° C. In order to increase the absorption capacity of the absorbent, the water and temperature of the fluid stream is controlled so that the stream both entering and leaving the absorbent bed has a degree of saturation of at least 30%, but does not contain a separate liquid aqueous phase.

7 Claims, No Drawings

DESULPHURIZATION

This application is a continuation-in-part of application Ser. No. 06/876,747, filed June 20, 1986, now pending; and a continuation-in-part of application Ser. No. 06/889,464, filed July 25, 1986, now U.S. Pat. No. 4,717,552.

This invention relates to desulphurisation and in particular to the removal of sulphur compounds such as hydrogen sulphide from fluid, ie gaseous or liquid, feedstock streams, particularly hydrocarbon streams such as natural gas. Such streams often contain substatial amounts of sulphur compounds, for example, where the hydrocarbon is gaseous, in an excess of 50 ppm by volume expressed as equivalent hydrogen sulphide.

Before use it is generally desirable to reduce the sulphur compounds content of the feedstock to a low level, for example to below 10 ppm by volume. One method of sulphur compound removal that is commonly employed is to contact the feedstock stream with a bed of particles of a suitable absorbent, such as zinc oxide. While a product stream of low sulphur content can be produced, such absorbents have only a limited capacity at low absorption temperatures and so, if large quantities of sulphur compounds have to be removed, the beds need frequent replenishment.

We have found that the low absorption temperature capacity of certain zinc oxide-containing absorbents can be significantly improved if the feedstock contains a proportion of water.

It has been proposed in GB-A-1568703 to adjust the water vapour content of a synthesis gas stream, ie a gas stream containing hgydrogen and carbon oxides, to 0.5 to 5% by volume prior to desulphurisation with a zinc oxide bed. In this reference the desulphurisation is preferably effected at temperatures above 200° C. The object of incorporation of water vapour in the gas stream used in the process of that reference was to supress the formation of sulphur compounds such as carbonyl sulphide and carbon disulphide which are less readily removed than hydrogen sulphide from gas streams. Such compounds presumably result from the reactions:

$$H_2S + CO_2 \rightarrow H_2O + COS$$

$$H_2S + COS \rightarrow H_2O + CS_2$$

These reactions are reversible and so the formation of carbonyl sulphide and carbon disulphide is supressed by the incorporation of water in the gas stream. However the rate of such reactions is believed to be very small at low temperatures and so carbonyl sulphide and carbon disulphide formation is unlikely to be a problem when effecting desulphurisation at low temperatures. The above reference has no appreciation that the presence of a controlled amount of water in the gas stream has the effect of increasing the absorption capacity of zinc oxide beds when operating at low absorption temperatures, and indeed suggests that the presence of water would be expected to be undesirable in view of the fact that the hydrogen sulphide absorption reaction produces water according to the equation $$H_2S + ZnO \rightarrow ZnS + H_2O$$

and so the presence of water might be expected to inhibit hydrogen sulphide absorption.

Accordingly the present invention provides a process for the removal of hydrogen sulphide from a fluid stream comprising passing the fluid stream, at a temperature below 120° C., preferably below 80° C., particularly below 50° C., through a bed of a particulate zinc oxide-containing absorbent having a surface area above 50 $m^2.g^{-1}$, and controlling the water content and the temperature of the fluid stream such that the degree of saturation of the fluid stream with water is at least 30%, preferably above 50%, particularly above 80%, both as it enters and leaves the bed, but is such that there is no separate liquid aqueous phase in the stream entering and leaving the bed.

The particulate absorbent material preferably comprises at least 60%, especially at least 80%, by weight of zinc oxide, calculated on the constituents of the absorbent material non-volatile at 90° C. As used in the process the zinc oxide may be, at least initially, wholly or partly hydrated or in the form of a salt of a weak acid, eg a carbonate, or basic carbonate.

The absorbent material is preferably in the form of porous agglomerates, as may be made, for example, by mixing a finely divided zinc oxide composition with a cement binder and a little water, insufficient to give a slurry, and then granulated or extruded. In order to aid access of the heated gas stream into the particles, the latter may be provided in the form of extruded pellets having a plurality of through passages. Typically the BET surface area of the particles is at least 50, preferably in the range 70 to 200, $m^2.g^{-1}$, and the pore volume of the particles is preferably at least 0.2 $cm^3.g^{-1}$.

Since the absorption efficiency and hence the life of a zinc oxide particulate bed depends on the rate of diffusion of the zinc sulphide formed by reaction of the zinc oxide with the sulphur compounds towards the interior of the particle, particularly at low absorption temperatures, it is preferable to employ zinc oxide particles having a high pore volume, above 0.2 $cm^3.g^{-1}$, and high surface area, above 50 $m^2.g^{-1}$. With zinc oxide particles having a lower pore volume and a surface area of the order of 25 to 30 $m^2.g^{-1}$ the effect of water enhancing the absorption capacity is not nearly so significant and so the bed life at low absorption temperatures is relatively low, necessitating the use of large bed volumes to avoid premature break-through the sulphur compounds into the product stream. By using a bed of particles of pore volume above, for example, 0.25 $cm^3.g^{-1}$ and surface area above, for example, 70 $m^2.g^{-1}$, the bed volume can be markedly reduced, eg to about one third of that required with particles of low pore volume and surface area 25 to 30 $m^2.g^{-1}$. The particles employed thus preferably have a surface area above 70 $m^2.g^{-1}$ and a pore volume above 0.25 $cm^3.g^{-1}$.

Preferred particulate absorbent materials for the process have a hydrogen sulphide absorption capacity of at least 20%, especially at least 25%, of the theoretical, at a temperature of 25° C., as determined in a standard test in which a mixture of hydrogen sulphide (2000 ppm by volume), carbon dioxide (4% by volume), and methane (balance) is passed through a bed of the particles at atmospheric pressure and a space velocity of 700 $h^{-1}$ using a bed of circular cross section having a length to diameter ratio of 5.

A particularly suitable particulate zinc oxide material is that sold by Imperial Chemical Industries plc as "Catalyst 75-1". These particles are granules typically having a surface area of the order of 80 $m^2.g^{-1}$ and a pore volume of about 0.5 cm$^3$.g$^{-1}$, and an adsorption capacity of about 27% of theoretical when measured by the above procedure.

Alternatively the particulate absorbent may comprise agglomerates of particles of an intimate mixture of oxides, hydroxides, carbonates and/or basic carbonates of copper, and zinc and/or at least one element such as aluinium as described in our copending European patent application 87303155.3 corresponding to U.S. Ser. No. 39070.

The inlet feedstock stream may be any gaeous or liquid that does not react with the absorbent. For example it may be a hydrocarbonstream, such as natural gas or naphtha, and typically contains hydrocarbons containing an average of up to ten carbon atoms. Natural gas usually will contain, in addition to methane, one or more of ethane, propane, propene, butanes, and butenes. The invention is also of utility with other feedstocks, for example air, carbon dioxide, halogenated hydrocarbons, eg chloro- and/or fluoro-carbons, phenols, or the product of fractionating a gas mixture produced by cracking or hydrocracking a normally liquid hydrocarbon feedstock, or the gaseous by-product of a zeolite-catalysed conversion of a feedstock such as methanol to gasoline. Preferably the fluid stream is substantially free from hydrogen and carbon monoxide.

The sulphur compounds initially present in the feedstock stream usually include hydrogen sulphide and/or carbonyl sulphide, and possibly carbon disulphide, methyl mercaptan, diethyl sulphide, and/or tetrahydrothiophene. The total initial concentration of hydrogen sulphide and/or of sulphur compounds readily hydrolysable thereto and expressed as sulphur equivalent hydrogen sulphide, is typically in the range 10 to 1000 ppm by volume of the feedstock when the latter is in the gaseous phase. The absorption can be conducted so that a substantial proportion, eg over 75% by volume of the hydrogen sulphide, and of sulphur compounds readily hydrolysable thereto, can be removed. Typically the sulphur compounds content of the product is under 10, for example under 5, ppm by volume, expressed as above, but this is a matter of design, depending on the user's requirements.

In the process of the invention the temperature of the feedstock is typically in the range $-10°$ to $+120°$ C. Where the feedstock contains insufficient water, water may be added by contacting the feedstock with liquid water, eg by passage through a saturator, prior to passage through the particulate absorbent bed. Generally, it is preferred to employ a feedstock having a temperature somewhat below the desired absorption temperature and to saturate it at that lower temperature, which is preferably about 3° to 10° C. below the desired absorption temperature, and to heat the resultant saturated gas stream to the desired absorption temperature, thereby reducing its degree of saturation to below 100%. Alternatively steam may be injected into the feedstock to add water and to increase the temperature.

The temperature of the fluid stream should be controlled so that the degree of saturation, ie relative humidity where the feedstock is gaseous, both of the fluid stream entering and leaving the absorbent bed, is above 30%, preferably above 50%, particularly above 80%, more particularly above 90%, and most preferaly above 95%, but is such that no separate liquid aqueous phase is present in either stream. The reason for wishing to avoid the presence of a separate liquid aqueous phase is that pores of the high surface area absorbent materials tend to become blocked by the presence of liquid water hence restricting the access of the fluid stream to the absorbent material. Since, as described above, the absorption process produces water, it is important that not only is the water content of the fluid stream entering the bed of particulate absorbent such that no separate liquid aqueous phase is present, but also that the inlet water content is sufficiently low that a separate liquid aqueous phase will not result in the fluid stream leaving the absorbent bed. On the other hand the fluid entering, and leaving, the bed should have a high degree of saturation in order that the benefits of increased absorption capacity of the bed are realised.

In some cases it may be desirable to provide the bed with heating means so that the temperature thereof increases as the fluid stream passes through the bed. In this way the inlet and outlet degrees of saturation can be maintained closer to 100%. Alternatively it may be desirable to employ a plurality of absorbent beds in series and to provide for partial drying of the fluid stream, eg by means of a suitable adsorbent such as alumina or a molecular sieve, between beds in order to avoid the deposition of a liquid aqueous phase.

The amount of water that the fluid contains at any given degree of saturation will of course depend on the temperature and, in the case of gaseous feedstocks, also on the pressure. It is preferred that the fluid stream has a pressure from 0.5 to 120, particularly 1 to 100, bar abs.

The desulphurised fluid stream may be dried by means of a suitable absorbent, eg alumina or a molecular sieve, downstream of the particulate absorbent bed.

Without wishing to be limited it is thought that a possible explanation of the increase in absorption capacity of the bed resulting from the presence of a controlled amount of water in the fluid stream is that the reaction mechanism for the absorption of hydrogen sulphide by zinc oxide at low temperatures may involve the hydration of the surface layers of the zinc oxide, indicated in a simplistic form by the following equations $$ZnO + H_2O \rightarrow Zn(OH)_2$$

$$Zn(OH)_2 + H_2S \rightarrow ZnS + 2H_2O$$

in preference to the previously quoted equation $$ZnO + H_2S \rightarrow ZnS + H_2O$$

which is the prevalent mechanism at high temperatures and which proceeds only slowly at low temperatures. The presence of the hydroxyl groups may enhance the solid state diffusion reactions involved in the formation of zinc sulphide.

The invention is illustrated by the following examples.

EXAMPLE 1

Granules of size approximately 3 to 5 mm of ICI "Catalyst 75-1" were charged to a tube of internal diameter 2.54 cm to form a vertical bed of length 12 cm. The bed thus had a volume of about 60 ml. Natural gas, substantially at atmospheric pressure and containing 1% by volume of hydrogen sulphide and 120 ppm by volume of water, was saturated by bubbling through water at 25° C. The resultant gas thus contained about 2.5% v/v water and was then passed down through the bed maintained at about 30° C. and atmospheric pressure at a rate of 700 ml/min, (ie space velocity 700 hr$^{-1}$).

The hydrogen sulphide content of the gas leaving the bed was monitored and when it rose to 1–2 ppm by volume, indicating that hydrogen sulphide "break-through" had occured, the flow of gas was stopped and the absorbent discharged from the bed.

The absorbent was discharged in six equal parts A to F, so that the distribution of sulphur down the depth of the bed could be determined, and each part analysed, after drying at 105° C., for its sulphur content. The results are shown in the following table.

The experiment was repeaed but omitting the saturation step so that the gas stream contained only about 120 ppm by volume of water.

| Bed portion | Sulphur content of discharged absorbent (% w/w) | |
| --- | --- | --- |
| | 2.5% H$_2$O | 120 ppm H$_2$O |
| A (top) | 16.4 | 8.7 |
| B | 15.2 | 9.2 |
| C | 13.2 | 9.3 |
| D | 11.0 | 8.7 |
| E | 5.9 | 5.1 |
| F (bottom) | 1.1 | 1.3 |
| Average | 10.5 | 7.0 |
| Time to "break-through" | 6.25 hours | 4 hours |

It is seen that saturation of the gas stream at 25° C. thus increased the capacity of the absorbent bed before "break-through" ocurred by about 50%.

In a comparative example the gas stream was passed through a dessicant prior to passage through the absorbent bed: the results obtained were virtually identical with those quoted above for the gas containing 120 ppm of water.

EXAMPLE 2

The experiments of example 1 were repeated using gas streams containing 0.5% v/v hydrogen sulphide. The results are shown in the following table:

| Bed portion | Sulphur content of discharged absorbent (% w/w) | |
| --- | --- | --- |
| | 2.5% H$_2$O | 120 ppm H$_2$O |
| A (top) | 19.7 | 8.4 |
| B | 18.2 | 9.0 |
| C | 15.6 | 8.7 |
| D | 11.6 | 8.2 |
| E | 5.8 | 4.5 |
| F (bottom) | 1.1 | 1.0 |
| Average | 12.0 | 6.6 |
| Time to "break-through" | 13.5 hours | 6.5 hours |

It is seen that in this case the capacity of the bed before "break-through" occurred was increased by about 82% by the presence of 2.5% water.

EXAMPLE 3

The procedure of Example 1 was repeaed using a gas stream containing 5% v/v hydrogen sulphide. In this example passage of the gas through the absorbent bed was continued for 25 hours, regardless of "break-through", in order to determine the quantity of hydrogen sulphide that the bed could absorb. The results were as follows:

| Bed portion | Sulphur content of discharged absorbent (% w/w) | |
| --- | --- | --- |
| | 2.5% H$_2$O | 120 ppm H$_2$O |
| A (top) | 24.7 | 11.5 |
| B | 23.4 | 12.4 |
| C | 22.9 | 12.6 |
| D | 22.9 | 13.1 |
| E | 22.2 | 13.2 |
| F (bottom) | 23.3 | 14.0 |
| Average | 23.2 | 12.8 |

Again it is seen that the presence of 2.5% water in the gas stream resulted in an increase in the capacity of the absorbent bed of about 81%.

In a similar experiment wherein the water content of the gas stream was only 1% v/v, the increase in bed capacity was only about 30%.

In similar experiments performed with an absorbent bed temperature of 150° C. the increase in capacity of the absorbent bed given by the incorporation of about 2.5% v/v water was only about 8%.

EXAMPLE 4

The procedure of Example 2 was repeated using differing absorption temperatures and differing degrees of saturation. In this case the sulphur content of that part of the bed having the greatest sulphur content is quoted in the following table:

| Absorption temperature (°C.) | Relative humidity at absorption temperature (%) | Maximum sulphur content (% w/w) |
| --- | --- | --- |
| 5 | 0.3* | 10.0 |
| 5 | 100 | 17.5 |
| 25 | 0.4* | 9.0 |
| 25 | 33 | 12.5 |
| 25 | 65 | 16.0 |
| 25 | 95 | 20.0 |
| 70 | 0.03* | 10.1 |
| 70 | 10* | 15.5 |
| 70 | 100 | 23.0 |
| 150 | 0.02* | 17.5 |
| 150 | 0.66* | 20.0 |
| 150 | 10.6* | 26.5 |

*Comparative

It is seen that by having a high relative humidity the peak sulphur content obtained at low absorption temperatures could be increased to a novel approaching that achievable at high absorption temperatures.

EXAMPLE 5

The procedure of Example 2 was repeaed using, instead of the "ICI Catalyst 75-1", agglomerates made by mixing precipitates obtained by precipitating copper, zinc and aluminium compounds as basic carbonates and/or hydroxides with calcium aluminate cement and a little water, granulating the resultant mixture, and drying and calcining the resultant granules for 4 hours at 350° C. to convert the basic carbonates and hydroxides to oxides. The calcined granules had a density of 1.1 g.cm$^{-3}$, a BET surface area of 105 m$^2$.g$^{-1}$, and an approximate Cu:Zn:Al atomic proportion of 51:26:23. In this example the "dry" gas contained about 20 ppm of water and the saturation and absorption temperature was 23° C.

The results were as set out in the following table:

| Bed portion | Sulphur content of discharged absorbent (% w/w) | |
|---|---|---|
| | wet gas | dry gas |
| A (top) | 16.9 | 8.5 |
| B | 16.2 | 8.5 |
| C | 14.9 | 8.0 |
| D | 14.6 | 8.8 |
| E | 8.0 | 4.7 |
| F (bottom) | 1.3 | 0.6 |
| Average | 12.0 | 6.4 |
| Time to "break-through" | 10.3 hours | 5.9 hours |

EXAMPLE 6

Granules of size approximately 3 to 5 mm of ICI "Catalyst 75-1" were charged to a tube of internal diameter 2.54 cm to form a vertical bed of length 18 cm. The bed thus had a volume of about 90 ml. Natural gas at 30 bar abs. and containing about 0.1% by volume of hydrogen sulphide, 2% by volume of hydrogen, and 180 ppm by volume of water, was saturated by bubbling through water at 23° C. The resultant gas thus contained about 1100 ppm by volume of water and was then passed down through the bed maintained at about 23° C. at a rate corresponding to a space velocity of 1000 hr$^{-1}$ (expressed at 1 bar abs. and 23° C.).

The hydrogen sulphide content of the gas leaving the bed was monitored and when it rose to about 1 ppm by volume, indicating that hydrogen sulphide "breakthrough" had occurred, the flow of gas was stopped and the absorbent discharged from the bed.

The absorbent was discharged in six equal parts A to F, so that the distribution of sulphur down the depth of the bed could be determined, and each part analysed for its sulphur content. The results are shown in the following table.

The experiment was repeated but omitting the saturation step so that the gas stream was "dry" gas containing only about 180 ppm by volume of water.

| Bed portion | Sulphur content of discharged absorbent (% w/w) | |
|---|---|---|
| | wet gas | dry gas |
| A (top) | 16.0* | 13.1 |
| B | 28.0 | 13.0 |
| C | 27.2 | 10.6 |
| D | 22.6 | 10.6 |
| E | 18.2 | 8.6 |
| F (bottom) | 8.8 | 7.1 |
| Average | 20.1 | 10.5 |
| Time to "break-through" | 156 hours | 77 hours |

*It is believed that the low figure for the top of the bed results from liquid water entering the bed and blocking the pore of the top part of the bed.

Again it is seen that the use of "wet" gas greatly increased the absorption capacity of the bed.

I claim:

1. A process for the removal of hydrogen sulphide from a gaseous stream comprising passing the gaseous stream at a temperature below 120° C. through a bed of a particulate zinc oxide-containing absorbent having a surface area above 50 m$^2$.g$^{-1}$, characterised by controlling the water content and the temperature of the gaseous stream such that the degree of saturation of the gaseous stream with water is at least 30%, both as it enters and leaves the bed, but is such that there is no separate liquid aqueous phase in the stream entering and leaving the bed.

2. A process according to claim 1 wherein the gaseous stream is natural gas.

3. A process according to claim 1 wherein the gaseous stream is substantially free from hydrogen and carbon monoxide.

4. A process according to claim 1 wherein the water is added by contacting the gas with liquid water so as to saturate the gas and then increasing the temperature of the gas by 3°–10° C. prior to contact of the gas with the absorbent.

5. A process according to claim 1 wherein the absorption temperature is below 50° C.

6. A process according to claim 1 wherein the degree of saturation of the gaseous stream entering and leaving the bed is above 80%.

7. A process according to claim 1 wherein the absorbent comprises porous agglomerates having a pore volume of at least 0.25 cm$^3$.g$^{-1}$ and a surface area above 70 m$^2$.g$^{-1}$.

* * * * *